United States Patent
Manstein et al.

(10) Patent No.: US 12,121,475 B2
(45) Date of Patent: Oct. 22, 2024

(54) LOCALIZED COOLING TO INDUCE BROWNING OF ADIPOSE TISSUE

(71) Applicant: THE GENERAL HOSPITAL CORPORATION, Boston, MA (US)

(72) Inventors: Dieter Manstein, Coral Gables, FL (US); Michael Evers, Cambridge, MA (US); Nunciada Salma, Bolton, MA (US)

(73) Assignee: THE GENERAL HOSPITAL CORPORATION, Boston, MA (US)

(*) Notice: Subject to any disclaimer, the term of this patent is extended or adjusted under 35 U.S.C. 154(b) by 510 days.

(21) Appl. No.: 17/430,761

(22) PCT Filed: Feb. 13, 2020

(86) PCT No.: PCT/US2020/018182
§ 371 (c)(1),
(2) Date: Aug. 13, 2021

(87) PCT Pub. No.: WO2020/168124
PCT Pub. Date: Aug. 20, 2020

(65) Prior Publication Data
US 2022/0133531 A1 May 5, 2022

Related U.S. Application Data

(60) Provisional application No. 62/804,867, filed on Feb. 13, 2019.

(51) Int. Cl.
| | |
|---|---|
| *A61F 7/12* | (2006.01) |
| *A61F 7/00* | (2006.01) |
| *A61F 7/02* | (2006.01) |

(52) U.S. Cl.
CPC ........ *A61F 7/12* (2013.01); *A61F 2007/0009* (2013.01); *A61F 2007/0022* (2013.01);
(Continued)

(58) Field of Classification Search
CPC .............................. A61F 2007/0029
See application file for complete search history.

(56) References Cited

U.S. PATENT DOCUMENTS

| | | | |
|---|---|---|---|
| 8,968,377 B2 | 3/2015 | Boyden et al. | |
| 9,656,056 B2 * | 5/2017 | Boyden | A61F 7/02 |

(Continued)

FOREIGN PATENT DOCUMENTS

| | | |
|---|---|---|
| EP | 3173042 A1 | 5/2017 |
| EP | 3342379 A1 | 7/2018 |

OTHER PUBLICATIONS

Loap, Suvaddhana, and Richard Lathe. "Mechanism underlying tissue cryotherapy to combat obesity/overweight: triggering thermogenesis." Journal of obesity 2018 (2018).

(Continued)

*Primary Examiner* — Kaitlyn E Smith
(74) *Attorney, Agent, or Firm* — Tarolli, Sundheim, Covell & Tummino LLP

(57) ABSTRACT

Described are methods for inducing browning of adipose tissue. More specifically, the present disclosure relates generally to methods for inducing browning of adipose tissue remote to the treatment location. The methods can include at least a first treatment and a second treatment, wherein the treatments comprise applying a cooling element to a local adipose tissue deposit, wherein the cooling element cools the local adipose tissue deposit to a temperature of between 0° C. to 30° C. for a period of time sufficient to induce browning of adipose tissue in one or more areas of the subject's body remote to the local adipose tissue deposit.

23 Claims, 11 Drawing Sheets

(52) U.S. Cl.
CPC . *A61F 2007/0023* (2013.01); *A61F 2007/004* (2013.01); *A61F 2007/0075* (2013.01); *A61F 2007/029* (2013.01); *A61F 2007/126* (2013.01)

(56) References Cited

U.S. PATENT DOCUMENTS

| | | | | |
|---|---|---|---|---|
| 2012/0296402 | A1* | 11/2012 | Kotter | A61F 7/10 607/108 |
| 2015/0119849 | A1* | 4/2015 | Aronhalt | A61F 7/10 607/113 |

OTHER PUBLICATIONS

Wang, Tse-Yao, et al. "Intermittent cold exposure improves glucose homeostasis associated with brown and white adipose tissues in mice." Life sciences 139 (2015): 153-159.

International Search Report for corresponding Application Serial No. 2020025114, Dated Jun. 15, 2020, pp. 1-7.

* cited by examiner

ABBREVIATIONS
isWAT: interscapular white adipose tissue (WAT)
triWAT: triceps-associated WAT
asWAT: anterior subcutaneous WAT
ingWAT: inguinal WAT

LOCALIZED COOLING INDUCES SYSTEMIC BROWNING OF WHITE ADIPOSE TISSUE

ABBREVIATIONS
isWAT: interscapular white adipose tissue (WAT)
triWAT: triceps-associated WAT
asWAT: anterior subcutaneous WAT
ingWAT: inguinal WAT

LOCALIZED COOLING INDUCES
BROWNING OF WHITE ADISPOSE TISSUE

ABBREVIATIONS
isWAT: interscapular white adipose tissue (WAT)
triWAT: triceps-associated WAT
asWAT: anterior subcutaneous WAT
ingWAT: inguinal WAT

LOCALIZED COOLING TO INDUCE BROWNING OF ADIPOSE TISSUE

RELATED APPLICATIONS

This application claims the benefit of U.S. Provisional Application No. 62/804,867, entitled "SELECTIVE CRYO-LIPOLYSIS INDUCES BROWNING OF WHITE ADIPOSE TISSUE," filed Feb. 13, 2019. The entirety of this application is hereby incorporated by reference for all purposes.

TECHNICAL FIELD

The present disclosure relates generally to methods for inducing browning of adipose tissue and recruitment of brown and beige fatty tissue and induction of related physiological changes. More specifically, the present disclosure relates generally to methods for inducing browning of adipose tissue remote to the treatment location.

BACKGROUND

Obesity and metabolic diseases are a growing concern worldwide. Since 1980, the number of obese people worldwide has more than doubled. Obesity is a chronic condition thought to be caused by excess energy intake, relative to energy expenditure which leads to weight gain. People with obesity are at risk for developing metabolic syndrome. Metabolic syndrome is a group of risk factors, such as central obesity (excess accumulation of fat in the abdominal area, particularly due to visceral fat), insulin resistance, dyslipidemia, and hypertension that increase the likelihood of developing cardiovascular disease, stroke, type 2 diabetes, and certain cancers. Because risk factors for obesity and metabolic syndrome are linked, one approach to reverse the risk of obesity and metabolic syndrome is to decrease energy intake and increase energy expenditure.

Brown adipose tissue (BAT) is a highly metabolic form of fat tissue that natively exists in humans and other mammals. The primary function of BAT is to convert chemical energy to heat through a highly metabolic process of uncoupled respiration (non-shivering thermogenesis), which is mediated by the uncoupled protein 1 (UCP1) expressed in brown adipose cells. It has been found that defective or insufficient BAT is associated with obesity. The amount of BAT present in humans correlates strongly with lower body fat levels and healthy metabolism.

It has been found that beige adipocytes induced by browning of adipose tissue are phenotypically similar to the classical brown adipocytes in BAT. Specifically, beige adipocytes have many mitochondria, multilocular lipid droplets, and they express UCP1. It has been suggested that beige adipocytes may contain comparable amounts of UCP1 to BAT, indicating that they may have similar thermogenic capacities.

Thus, there is a need to identify new methods of browning adipose tissue that can be used to modulate metabolism and/or to treat obesity and metabolic disorders.

SUMMARY

The present disclosure relates generally to methods for inducing browning of adipose tissue and, more particularly, to methods for inducing browning of adipose tissue remote to the treatment location.

In one aspect, the present disclosure can include a method of inducing remote browning of adipose tissue in a subject comprising carrying out a plurality of treatments on the subject wherein the treatments comprise at least a first treatment and a second treatment, wherein the first treatment comprises cooling a first local adipose tissue deposit to a temperature of between 0° C. to 30° C. for a first period of time sufficient to induce browning of adipose tissue in one or more areas of the subject's body remote to the first local adipose tissue deposit; and wherein the second treatment comprises cooling a second local adipose tissue deposit to a temperature of between 0° C. to 30° C. for a second period of time sufficient to induce browning of adipose tissue in one or more areas of the subject's body remote to the second local adipose tissue deposit, wherein the first and second local adipose tissue deposits are the same or are different, and wherein the second treatment is carried out 2-30 days after the day that the first treatment is carried out. In a further aspect, the method is carried out an indefinite number of times until a desired effect or a predetermined outcome is achieved and/or maintained.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 5(a) is an image of the mouse hair removal; FIG. 5(b) is an image of tattoos applied to the inguinal area of the mouse; FIG. 5(c) is an image of the cooling treatment applied to the inguinal area of the mouse; FIG. 5(d) is an image of the cooling system including the thermoelectrical recirculating chiller, thermal controller, cooling probe, and cooling probe diameter; FIG. 5(e) is a graph showing the cooling probe setting and temperature measurements; and FIG. 5(f) is a graph showing the mouse body temperature measurements.

FIG. 6(a) provides images of Ucp1 expression in the treated and untreated (i.e., contralateral) inguinal (ING) fat pads; FIG. 6(b) provides images of Ucp1 expression in treated and untreated epididymal (EPI) fat pads and untreated BAT fat pads; and FIG. 6(c) provides images of Ucp1 expression in the untreated retroperitoneal (RETRO) fat pad;

FIG. 7(a) is a graph showing Ucp1 levels in the ING fat pad; FIG. 7(b) is a graph showing Ucp1 levels in the EPI fat pad; and FIG. 7(c) is a graph showing Ucp1 levels in the BAT fat pad;

DETAILED DESCRIPTION

Definitions

Figure 1:
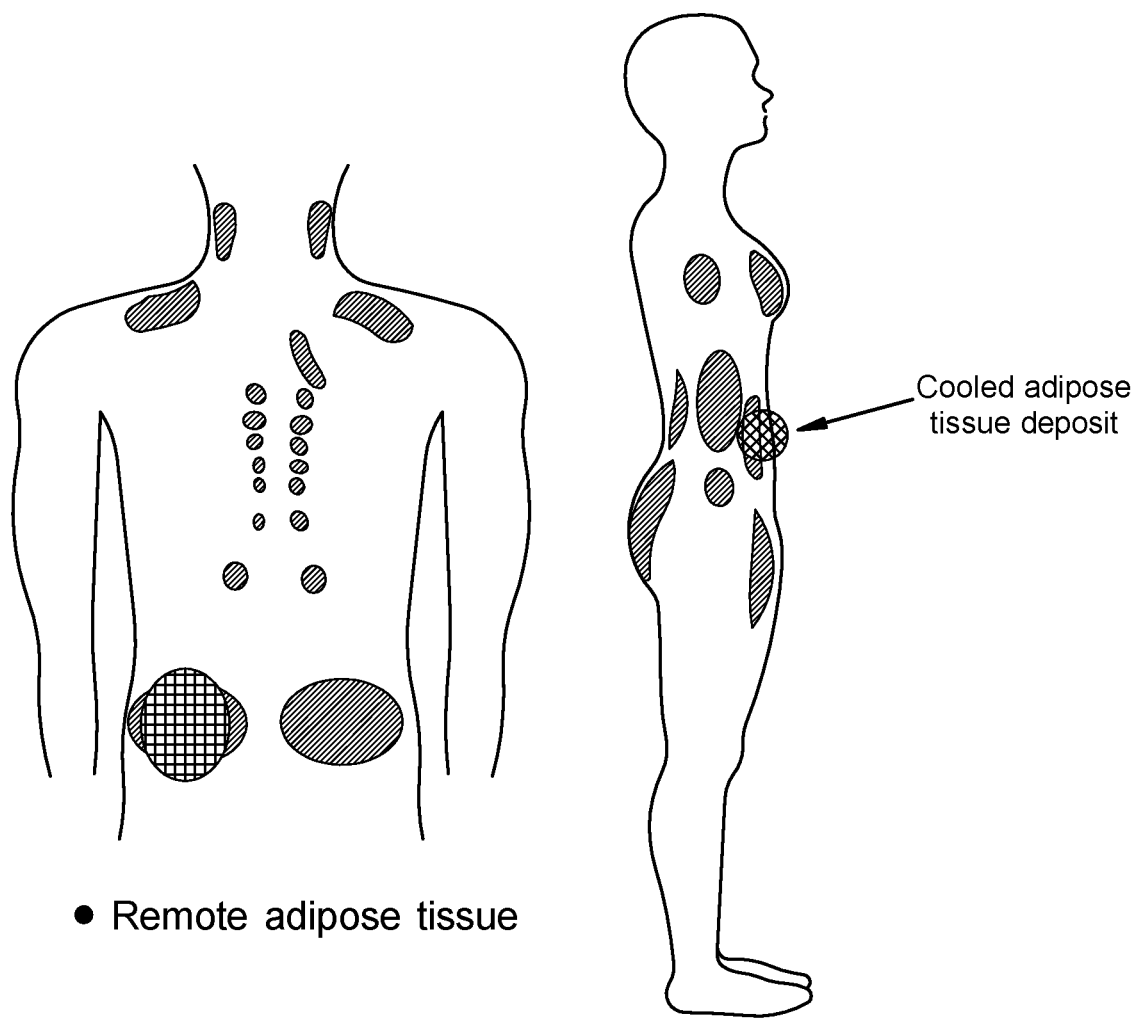
FIG. 1 provides a diagram illustrating remote adipose tissue deposits relative to a cooled adipose tissue deposit in accordance with an aspect of the present disclosure (each of the regions in grey correspond to exemplary remote adipose tissue deposits)

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

Unless otherwise indicated, all numbers expressing quantities used in the specification and claims are to be understood as being modified in all instances by the term "about." Accordingly, unless otherwise indicated, the numerical properties set forth in the following specification and claims are approximations that may vary depending on the desired properties sought to be obtained.

Notwithstanding that the numerical ranges and parameters setting forth the broad scope of the disclosure are approximations, the numerical values set forth in the specific examples are reported as precisely as possible. Any numerical values, however, inherently contain certain errors necessarily resulting from error found in their respective measurements.

Also herein, where a range of numerical values is provided, it is understood that each intervening value is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

As used herein, the term "brown adipose tissue" or "BAT" can refer to a heat-producing adipose tissue. BAT cells contain numerous small lipid vacuoles and a large number of well-developed mitochondria. BAT possesses the uncoupling protein UCP1 which, when activated, enables the rapid generation of heat and the oxidation of lipids and/or glucose. BAT is characterized by the ability to produce heat by non-shivering thermogenesis. BAT has a higher mitochondrial content and higher UCP1-expression as compared to WAT.

As used herein, the term "beige adipose tissue" can refer to discrete areas of UCP1-containing cells dispersed within white adipose tissue.

As used herein, the term "white adipose tissue" or "WAT" can refer to a heterogeneous tissue composed of lipid-filled adipocytes and several nonadipocyte cell populations, including endothelial, blood, uncharacterized stromal, and adipocyte precursor cells. WAT is the principal tissue for energy storage in humans. WAT plays an important role in whole body energy homeostasis. WAT stores excess energy in form of triglycerides, and releases fatty acids via lipolysis for usage by other organs.

As used herein, the term "sufficient to induce" can refer to the amount of time needed to bring about any detectable level of adipose tissue browning.

As used herein, the term "remote" can refer to an area of adipose tissue that lies outside the area of the adipose tissue deposit that was cooled (see e.g., FIG. 1).

As used herein, the terms "subject" and "patient" can be used interchangeably to refer to any warm-blooded living organism including, but not limited to, a human being, a rat, a mouse, a dog, a cat, a goat, a sheep, a horse, a monkey, an ape, a rabbit, a cow, etc.

As used herein, the term "plurality" refers to more than one.

As used herein, the term "UCP1" refers to uncoupling protein 1 found in humans, and the term "Ucp1" refers to uncoupling protein 1 found in mice. UCP1/Ucp1 is recognized as one example of a marker found in brown and beige adipose tissue.

Overview

The present disclosure relates generally to methods of inducing local and remote browning of adipose tissue. The present disclosure is based, at least in part, on the surprising finding that localized cold exposure can induce browning of adipose tissue in one or more areas of the body that is remote to the treatment location. It has also been discovered that remote browning of adipose tissue can continue for days after the cooling treatment is administered. By inducing browning of adipose tissue in areas remote to a treatment location, modulation of metabolism, weight loss and/or improved metabolic function can be achieved in a more effective manner, allowing for a more effective treatment of diseases and/or conditions such as obesity, cardiovascular disease, and metabolic disorders.

The methods disclosed in the present disclosure can vary from CoolSculpting®. The CoolSculpting system operates at temperatures below 0° C., which can freeze tissue. Additionally, with CoolSculpting, it can typically take at least four weeks to see fat loss, and it is recommended for subjects to wait at least one to two months before retreating an area. The methods disclosed in the present disclosure involve cooling adipose tissue to a temperature at or above 0° C. to avoid destroying the adipose tissue. The cooling treatments disclosed in the instant disclosure can also be carried out, for example, on a regular basis until a desired effect is achieved. The methods described in the present disclosure may not result in local fat loss, but may instead increase brown and beige fat mass.

Methods

In one aspect, the present disclosure includes a method of inducing remote browning of adipose tissue in a subject comprising carrying out a plurality of treatments on the subject. In one instance, the treatments can comprise at least a first treatment and a second treatment. In certain instances, the first treatment can comprise cooling a first local adipose tissue deposit to a temperature of between 0° C. to 30° C. for a first period of time sufficient to induce browning of adipose tissue in one or more areas of the subject's body remote to the first local adipose tissue deposit.

In further instances, the second treatment can comprise cooling a second local adipose tissue deposit to a temperature of between 0° C. to 30° C. for a second period of time sufficient to induce browning of adipose tissue in one or more areas of the subject's body remote to the second local adipose tissue deposit. In further instances, the first and second local adipose tissue deposits can be the same or are different. In even further instances, the second treatment can be carried out within 0-30 days after the day that the first treatment is carried out. In other instances, the treatments can comprise more than a first treatment and a second treatment. For example, in certain instances, an indefinite number of treatments can be carried out until a desired effect or a predetermined outcome is achieved.

One skilled in the art will appreciate that a variety of cooling elements can be used to cool localized adipose tissue deposits in accordance with the methods herein. In one aspect, the cooling element can be a cooling device or a cooling agent.

Exemplary cooling devices can contain thermal conductive materials, such as metals, metal plates, and glasses. In one instance, an exemplary cooling device may include one or more external non-invasive cooling units that can applied to the skin to proximately cool the adipose tissue deposit. For example, an exemplary cooling device can include a thermoelectric cooler. In certain instances, the cooling device can include a circulating cooling agent. Another exemplary cooling device can include one or more cooling probes that can be inserted directly into the adipose tissue deposit of the subject by piercing the skin of the subject. In further instances, a non-invasive cooling unit may also be used in conjunction with one or more probes. In another example, the non-invasive cooling unit may include other external cooling components including, for example, ice packs and evaporative materials that may be applied to the skin of the subject.

Exemplary cooling agents include liquids that can contain saline, glycerol, alcohol (e.g., menthol), or water/alcohol mixtures. In other instances the cooling agent can be ice or an ice slurry. Salts can be combined with liquid mixtures to obtain desired temperatures. In another instance, the cooling agent can be liquid nitrogen or cold air. Additionally, other cooling techniques, such as chemical reaction cooling, evaporative cooling, and the use of phase change materials, may be used to cool the adipose tissue deposit. The cooling agent may also comprise a phase change material that utilizes a phase change mechanism to extract heat.

The cooling element can be applied by all conventional methods known in the art. For example, the cooling element can be applied directly to the skin surface. In one instance, the cooling element can be topically applied to the skin surface in the form of e.g., a spray, gel, cream, or particulate solid material. In one instance, the cooling element can be applied by injection directly into the adipose tissue deposit. For example, the cooling element can be applied directly to the adipose tissue deposit and then either removed after contact or left in the adipose tissue deposit (e.g., injection of a liquid cooling agent or of small cooling particles, such as pellets or microbeads into the adipose tissue deposit). In one particular instance, a non-invasive or minimally invasive method (e.g., a superficial, laparoscopic or topical procedure not requiring invasive surgical techniques) can be used to cool a localized adipose tissue deposit.

The cooling element can be applied to one or more defined areas. In some instances, the cooling element can be applied to a single defined area. In other instances, the cooling element can be applied to more than one defined area. For example, in certain instances, a localized cooling treatment can be carried out where a first cooling element is applied to e.g., the abdomen, and a second cooling element is applied to e.g., the upper thighs. Spatial distribution of the cooling element can be controlled as needed. In some instances, the dimension of the surface area (e.g., where the cooling agent is in contact with the skin) can be as small as 1 $cm^2$ and as large as an adipose tissue deposit. In some instances, the surface area can be between 3 and 300 $cm^2$. Other surface area dimensions can be envisioned by one skilled in the art. Determination of the optimal surface area can be determined through routine variation of parameters.

The cooling element can follow the contour of the area to which it is applied. For example, a flexible device can be used to follow the contour of the surface area where cooling is applied. The device can also modify the shape of the contacted surface such that the surface is contoured around or within the cooling agent or the device containing the cooling agent upon contact. The cooling element can contact more than one surface at once, for example, when the surface is folded and contacted on either side by the cooling element. In one instance, the cooling element is shaped to enhance thermodynamic heat exchange ("thermal exchange") at the contacted surface (e.g., skin surface). In order to enhance conduction, a liquid, e.g., an antifreeze substance such as glycerol or the like, can be used at the interface between the cooling element and the contacted surface.

Where necessary, application of the cooling element can be coupled with use of a pain management agent, such as an anesthetic or analgesic (cooling alone has analgesic properties, thus use of additional pain management agents is optional). Local anesthetics, for example, can be topically applied at the point of contact either before, after or during application of the cooling element. Where necessary, systemic administration of the anesthetic can be provided through conventional methods, such as injection or oral administration.

The cooling element can be applied in a manner that results in the cooling of a local adipose tissue deposit to a desired temperature for a desired amount of time sufficient to induce browning of adipose tissue in one or more areas of the subject's body remote to the local adipose tissue deposit. One skilled in the art will appreciate that in certain instances the cooling element may start out at a warm temperature and then it can be cooled to a temperature that can be used to cool the local adipose tissue deposit to a desired temperature. In one particular example, the cooling element can be applied so that it results in the cooling of a local adipose tissue deposit to a temperature ranging between 0° C. to 30° C. for a period of at least 10 minutes.

In one aspect, the local adipose tissue deposit can be cooled to a temperature between 0° C. to 30° C. In one instance, the local adipose tissue deposit can be cooled to a temperature between 4° C. to 30° C. In another instance, the local adipose tissue deposit can be cooled to a temperature between 4° C. to 25° C. In a further instance, the local adipose tissue deposit can be cooled to a temperature between 10° C. to 25° C. In yet a further instance, the local adipose tissue deposit can be cooled to a temperature between 10° C. to 20° C. In other instances, the local adipose tissue deposit can be cooled to a temperature of 0, 1, 2, 3, 4, 5, 6, 7, 8, 9, 10 . . . 30° C.

In another aspect, the local adipose tissue deposit can be cooled so that the temperature of the local adipose tissue deposit oscillates between 0° C. to 30° C. In certain instances, the temperature of the local adipose tissue deposit can oscillate between 4° C. to 30° C., between 4° C. to 25° C., between 10° C. to 25° C., or between 10° C. to 20° C.

In some instances, the skin can be cooled to a temperature between −10° C. to 25° C. In certain instances, the skin can be cooled to a temperature between e.g., −5° C. to 25° C., 0° C. to 20° C., or 5° C. to 15° C. In other instances, the skin can be cooled to a temperature of −10, −9, −8, −7, −6, −5, −4, −3, −2, −1, 0, 1, 2, 3 . . . 25° C.

In another aspect, the local adipose tissue deposit can be cooled at the desired temperature for a period of at least 10 minutes. In certain instances, the local adipose tissue deposit can be cooled at the desired temperature for a period of between 10 minutes and 12 hours. In some instances, the local adipose tissue deposit can be cooled at the desired temperature for a period of between 10 and 15 minutes, between 10 and 20 minutes, between 10 and 30 minutes, between 10 and 40 minutes, and between 10 and 60 minutes. In one particular instance, the local adipose tissue deposit can be cooled at the desired temperature for 10 minutes or 15 minutes. In other instances, the local adipose tissue deposit can be cooled at the desired temperature for a period of 10, 11, 12, 13, 14, 15, 16, 17, 18, 19, 20 . . . 720 minutes.

In a further aspect, the localized cooling treatments described in the present disclosure can be carried out a plurality of times. For example, the localized cooling treatments can be carried out anywhere from 2 to an indefinite number of times. In some instances, the localized cooling treatments can be carried out 2, 3, 4, 5, 6, 7, 8, 9, 10 . . . 20 times.

In another aspect, the plurality of localized cooling treatments can be carried out such that there is between 0-30 days between each treatment (i.e., the treatments may or may not be carried out on consecutive days). In some instances, the plurality of localized cooling treatments can be carried out so that there is 0, 1, 2, 3, 4, 5, 6, 7, 8, 9, 10 . . . 30 days between each treatment (i.e., the treatments may or may not be carried out on consecutive days). In another aspect, a plurality of localized cooling procedures can be carried out, but not on consecutive days.

In a further aspect, the plurality of localized cooling treatments can be carried out such that there is between 0-90 days between each treatment (i.e., the treatments may or may not be carried out on consecutive days). In some instances, the plurality of localized cooling treatments can be carried out so that there is 0, 1, 2, 3, 4, 5, 6, 7, 8, 9, 10 . . . 90 days between each treatment (i.e., the treatments may or may not be carried out on consecutive days).

In certain instances, one or more localized cooling treatments may be carried out on the same day but on different adipose tissue deposits. In some instances, when more than one localized cooling treatment is carried out on the same day on different adipose tissue deposits, subsequent treatments can be carried out 1-90 days later on the same adipose treatment deposits (i.e., the treatments may or may not be carried out on consecutive days). In certain instances, when more than one localized cooling treatment is carried out on the same day on different adipose tissue deposits, subsequent treatments can be carried out 1-30 days later on the same adipose treatment deposits (i.e., the treatments may or may not be carried out on consecutive days). In certain instances, when more than one localized cooling treatment is carried out on the same day on different adipose tissue deposits, the same localized tissue deposit is not treated on consecutive days. In some instances, when more than one localized cooling treatment is carried out on the same day on different adipose tissue deposits, the same localized tissue deposit can be treated between, e.g., 2-30 or 2-90 days later (i.e., there is at least one day separating the treatment days).

In a further aspect, the plurality of localized cooling treatments can be carried out such that there is between 1-30 days between each treatment (i.e., there is at least one day separating the treatment days). In another aspect, the plurality of localized cooling treatments can be carried out such there is between 1-9 days or 2-6 days between each treatment. In other instances, the plurality of localized cooling treatments can be carried out so that there is 1, 2, 3, 4, 5, 6, 7, 8, 9, 10 . . . 30 days between each treatment (i.e., there is at least one day separating the treatment days).

In another aspect, the plurality of localized cooling treatments can be carried out such that there is between 1-90 days between each treatment (i.e., there is at least one day separating the treatment days). In other instances, the plurality of localized cooling treatments can be carried out so that there is 1, 2, 3, 4, 5, 6, 7, 8, 9, 10 . . . 90 days between each treatment (i.e., there is at least one day separating the treatment days).

In one instance, a first localized cooling treatment can be carried out followed by a second localized cooling treatment where the second treatment is carried out 1-30 days after the first treatment (i.e., the treatments may or may not be carried out on consecutive days). In another instance, a first localized cooling treatment can be carried out followed by a second localized cooling treatment where the second treatment is carried out 2-30 days after the first treatment (i.e., there is at least one day separating the first and second localized cooling treatments). In certain instances, the first and second localized cooling treatments can be carried out so that there is 0, 1, 2, 3, 4, 5, 6, 7, 8, 9, 10 . . . 30 days between the treatments (i.e., the first and second localized cooling treatments may or may not be carried out on consecutive days). In some instances, the first and second localized cooling treatments can be carried out so that there is 1, 2, 3, 4, 5, 6, 7, 8, 9, 10 . . . 30 days between the treatments (i.e., there is at least one day separating the first and second localized cooling treatments). In certain instances, the second localized cooling treatment can be carried out 2-10 days or 3-7 days after the first treatment.

In other instances, a plurality of localized cooling treatments can be carried out until a desired outcome is achieved. For example, a plurality of localized cooling treatments can be carried out until e.g., a desired weight loss goal is achieved, insulin resistance is improved, high cholesterol is lowered, high triglyceride levels are lowered, or high blood pressure is lowered. For example, a plurality of localized cooling treatments can be carried out until the body weight of the subject decreases by, e.g., 5, 6, 7, 8, 9, 10 . . . 60%. In another example, a plurality of localized cooling treatments can be carried out until a certain reduction in, e.g., waist or thigh circumference is achieved. In further examples, a plurality of localized cooling treatments can be carried out until the subject's metabolic health indicators, such as but not limited to, cholesterol levels, triglyceride levels, or blood pressure levels are considered in the normal range by a healthcare provider.

One skilled in the art will appreciate that a wide variety of treatment regimens are envisioned. For example, localized cooling treatments can be carried out on a frequent basis (e.g., every day, every other day, every three days . . . every ten days), until a desired result or predetermined outcome is achieved. Once the desired result or predetermined outcome is achieved, the localized cooling treatments can be carried out on a less frequent basis (e.g., every 20 to 90 days) in order to maintain the desired result.

In one instance, the plurality of localized cooling treatments can be carried out under the same conditions. For example, the plurality of the localized cooling treatments can each cool the same adipose tissue deposit to the same temperature for the same amount of time. In other instances, the plurality of localized cooling treatments can be carried out under different conditions wherein one or more treatment conditions are varied. Exemplary treatment conditions that can be varied include (i) the adipose tissue deposit location, (ii) the temperature that the adipose tissue is cooled to, (iii) the period of time that the adipose tissue deposit is subject to localized cooling, and (iv) the period of time between each localized cooling treatment.

One skilled in the art would recognize that any adipose tissue deposit can be subject to localized cooling in accordance with the methods of the present disclosure. Exemplary treatment regions can include the abdomen, supraclavicular region, dorsocervical or cervical region, flanks, buttocks, lower torso, hips, and thighs (e.g., upper thighs).

In one instance, the adipose tissue deposit selected for cooling can be determined on an individualized basis by scanning the subject using positron-emission tomography/X-ray computed tomography (PET-CT) imaging, tomography, thermography, or any other technique, as will be appreciated by a person skilled in the art.

Biomedical imaging and spectroscopy can be used to monitor the browning of adipose tissue. In certain instances, one or more of positron-emission tomography (PET), X-ray computed tomography, and magnetic resonance (MR) imaging and spectroscopy can be used to monitor the browning of adipose tissue. In one instance PET/CT with 2-deoxy-2-[$^{18}$F]fluoro-D-glucose can be used for imaging the browning of adipose tissue. In other instances, probe-based fluorescence lifetime imaging and probe-based optical coherence tomography can be used. In other instances, quantitative fat-water MRI can be used. In certain instances, biopsies can be taken of the adipose tissue. Techniques such as immunohistochemistry (IHC) analysis and polymerase chain reaction (PCR), e.g., real time quantitative PCR (q-PCR), can be used to analyze UCP1 levels in the biopsied samples. An increase in UCP1 expression can be attributed to the browning of adipose tissue. In other instances, extra cellular flux analysis can be performed to determine oxygen consumption rate and extra cellular acidification rate.

In one aspect, the methods described in the present disclosure can induce remote browning of adipose tissue. As described previously, the term "remote" can refer to one or more areas of adipose tissue that lie outside the area of adipose tissue that was cooled, as illustrated in FIG. 1. In one example, cooling an adipose tissue deposit located on the abdomen of the subject can result in the browning of adipose tissue in the e.g., hips and/or thighs of the subject. In another instance, cooling an adipose tissue deposit located at the supraclavicular area of the subject can result in the browning of adipose tissue in the e.g., upper back of the subject. In a further instance, cooling an adipose tissue deposit located on the right side of the abdomen of the subject can result in the browning of adipose tissue on the left side of the abdomen. One skilled in the art will appreciate that localized cooling in one treatment area can induce adipose tissue browning in multiple remote adipose tissue deposits. In one instance, localized cooling in one treatment area can induce systemic browning of adipose tissue throughout the body.

The methods described in the present disclosure can be used to treat certain diseases and/or conditions. One skilled in the art will appreciate that the methods described in the present disclosure can be used to treat any disease and/or condition in which an increase in browned adipose tissue would be beneficial. For example, the methods can be used to induce weight loss or to change a subject's metabolic rate, e.g., increase a subject's metabolic rate. The methods can also be used to treat obesity, cardiovascular disease, and diabetes (e.g., Type II diabetes). In other instances, the methods disclosed in the present disclosure can also be used to improve metabolic syndrome risk factors including increased blood pressure, insulin resistance, excess fat around the waist, high triglyceride levels, and hypercholesterolemia. In further instances, the methods disclosed in the present disclosure can be used to reduce visceral and/or subcutaneous fat. In other instances, the methods disclosed in the present disclosure can be used to combat the effects of aging. For example, the methods disclosed in the present invention can to reverse the postmenopause and post-andropause decline in metabolic rate that is accompanied by increased visceral adiposity.

One skilled in the art will appreciate that the methods of the present disclosure can be carried out in, for example, a medical clinic, a doctor's office, a spa, or at a subject's home using a consumer device.

Another aspect of the present disclosure includes a method of increasing brown and beige fat mass in a subject comprising carrying out a plurality of treatments on the subject. In one instance, the treatments can comprise at least a first treatment and a second treatment. In certain instances, the first treatment can comprise cooling a first local adipose tissue deposit to a temperature of between 0° C. to 30° C. for a first period of time sufficient to induce browning of adipose tissue in one or more areas of the subject's body remote to the first local adipose tissue deposit.

In further instances, the second treatment can comprise cooling a second local adipose tissue deposit to a temperature of between 0° C. to 30° C. for a second period of time sufficient to induce browning of adipose tissue in one or more areas of the subject's body remote to the second local adipose tissue deposit. In further instances, the first and second local adipose tissue deposits can be the same or are different. In even further instances, the second treatment can be carried out e.g., 1-30 days or 2-30 days, after the day that the first treatment is carried out. In other instances, the treatments can comprise more than a first treatment and a second treatment. For example, in certain instances, an indefinite number of treatments can be carried out until a desired effect or a predetermined outcome is achieved.

Systems

Figure 2:
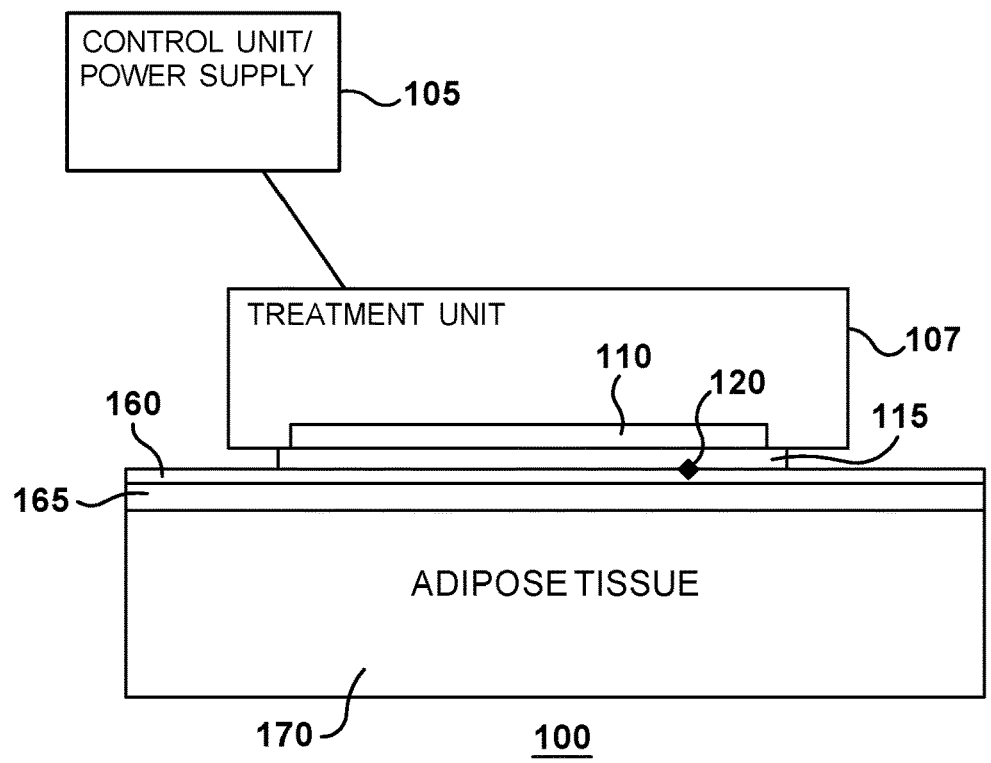
FIG. 2 provides a diagram illustrating a cooling system in accordance with an aspect of the present disclosure.

FIG. 2 illustrates a treatment system 100 for localized cooling of an adipose tissue deposit in accordance with an aspect of the present disclosure.

As shown in FIG. 2, treatment system 100 may include a control unit 105 and a treatment unit 107, which may include a cooling element 110 and a treatment interface 115. Treatment system 100 may include a number of configurations and instruments. Algorithms that are designed for different types of procedures, configurations and/or instruments may be included for control unit 105.

Control unit 105 may include a power supply, for example, control unit 105 may be coupled to a power source, for supplying power to treatment unit 107. Control unit 105 can also include a computing device having control hardware and/or software for controlling, based on inputted properties and/or parameters, cooling element 110 and treatment interface 115. In one instance, treatment interface 115 can include a detector 120 for, e.g., extracting temperature information from the epidermis 160, dermis 165 and/or adipose tissue 170 so that the temperature of the epidermis 160, dermis 165 and/or adipose tissue 170 can be controlled.

Treatment unit 107 may be a handheld device, an automated apparatus, and the like. Treatment unit 107 may be held in place using, e.g., a belt, a strap, adhesive patch, or other retention device. Cooling element 110 can include any type of cooling element described in the present disclosure, such as a thermoelectric cooler.

Treatment interface 115 can be any type of interface between cooling element 110 and the skin (wherein the skin is comprised of the epidermis 160 and dermis 165) for effecting cooling of adipose tissue 170. For example, treatment interface 115 may include a cooling (conductive) plate, a cooling fluid-filled vessel, a free-forming membrane (for a complementary interface with an uneven epidermis), a textile material, and the like. Preferably, treatment interface 115 comprises a heat conducting material that allows for maximum heat transfer between cooling element 110 and the adipose tissue 170. For example, treatment interface 115 can be a fluid-filled vessel or a membrane so that the change in pressure from cooling element 110 caused by a pulsing flow of cooling fluid may be transferred to the target tissue. Furthermore, treatment interface 115 may simply be a chamber where cooling fluid may be applied directly to the target adipose tissue 170.

Detector 120 can be a temperature monitor, for example, a thermocouple, a thermistor, and the like. Detector 120 may include any thermocouple type, including Types T, E, J, K, G, C, D, R, S, B, for monitoring and/or controlling tissue cooling. Detector 120 may also include a thermistor, which can comprise thermally-sensitive resistors whose resistances change with a change in temperature. The use of thermistors may be particularly advantageous because of their sensitivity. In one instance, a thermistor with a large negative temperature coefficient of resistance ("NTC") can be used. Preferably, a thermistor used for detector 120 may have a working temperature range inclusive of about −15° C. to 40° C. Furthermore, detector 120 can include a thermistor with active elements of polymers or ceramics. A thermistor used for detector 120 can be encapsulated in a protective material such as glass. Various other temperature-monitoring devices can also be used as dictated by the size, geometry, and temperature resolution desired. Detector 120 can also comprise an electrode which can be used to measure the electrical resistance of the skin surface area. Ice formation within superficial skin structures like the epidermis or dermis causes an increased electrical resistance. This effect can be used to monitor ice formation within the dermis. Detector 120 can further consist of a combination of several measurement methods.

Detector 120 can, thus, extract, inter alia, temperature information from the epidermis 160, dermis 165 and/or adipose tissue 170 as feedback to control unit 105. The detected temperature information can be analyzed by control unit 105 based on inputted properties and/or parameters. For example, the temperature of adipose tissue 170 may be determined by calculation based on the temperature of the epidermis 160 detected by detector 120. Thus, treatment system 100 may non-invasively measure the temperature of adipose tissue 170. This information may then be used by control unit 105 for continuous feedback control of treatment unit 107, for example, by adjusting the energy/temperature of cooling element 110 and treatment interface 115, thus maintaining optimal treatment temperature of adipose tissue 170 while leaving surrounding epidermis 160 and dermis 165 intact. Exemplary detectors include those known in the art that measure fat temperature and/or changes in tissue (e.g., skin or adipose tissue) rheology.

As described above, the cooling element 110 can provide adjustable temperatures in the range of about −10° C. up to 42° C. An automated temperature measurement and control sequence can be repeated to maintain such temperature ranges until a procedure is complete.

To further ensure that the epidermis 160 and/or the dermis 165 is not damaged by cooling treatment, an optical detector/feedback device can be used to monitor the change of optical properties of the epidermis (enhanced scattering if ice formations occur); an electrical feedback device can be used to monitor the change of electric impedance of the epidermis caused by ice formation in the epidermis; and/or an ultrasound feedback device may be used for monitoring ice formation (actually to avoid) in the skin. Feedback mechanisms can also be employed to monitor and control temperatures in the skin (i.e., dermis, epidermis or a combination thereof) or the adipose tissue. For example, a feedback mechanism can monitor the temperature of a subject's skin to ensure that the temperature therein in does not fall below a predetermined minimum temperature, for example, about −10° C. to about 25° C. In certain instances, a non-invasive feedback device can be externally applied to measure surface temperature at the point of contact and/or the surrounding region. In other instances, an invasive device, such as a thermocouple, can be used to measure internal temperatures. Feedback mechanisms can include all known in the art to monitor temperature and/or crystal formation. Crystal formation can be measured, for example by ultrasound imaging and acoustical, optical, and mechanical measurements. Mechanical measurements can include, for example, measurements of tensile strength. Any such device may include signaling control unit 105 to stop or adjust treatment to prevent tissue (e.g., skin or adipose tissue) damage.

It will be appreciated by one skilled in the art that the systems described in the present application can include instruments and devices that can detect the browning of adipose tissue. In certain instances, one or more of positron-emission tomography (PET), X-ray computed tomography, and magnetic resonance (MR) imaging and spectroscopy can be used in the systems. In one instance PET/CT with 2-deoxy-2-[$^{18}$F]fluoro-D-glucose can be used, and in other instances, probe-based fluorescence lifetime imaging and probe-based optical coherence tomography can be used in the systems.

Figure 3:
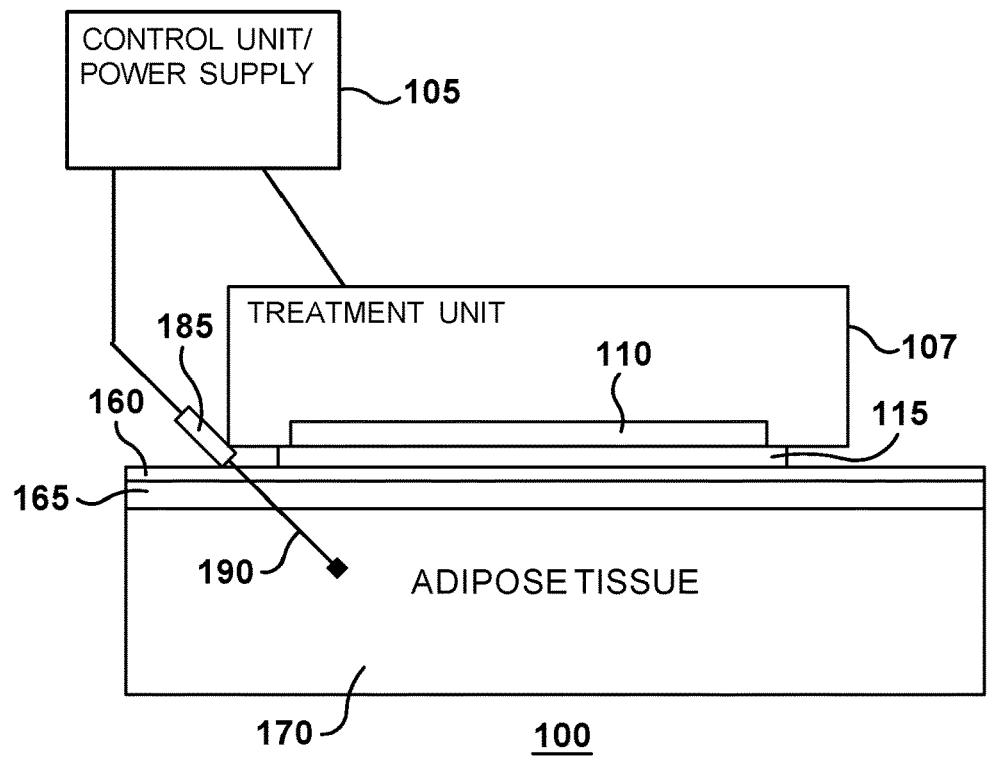
FIG. 3 provides a diagram illustrating a second cooling system in accordance with another aspect of the present disclosure.

As shown in FIG. 3, treatment system 100 may include a probe controller 185 and a probe 190 for minimally invasive cooling of adipose tissue 170. In one instance, the probe 190 can also be configured to carry out temperature measurements of adipose tissue 170. In another instance, probe 190 can be used to carry out minimally invasive cooling of the adipose tissue 170, and a second probe can be used to carry out temperature measurements of the adipose tissue 170. Exemplary probes include Peltier based probes, thermoelectric probes, single phase probes such as cold saline filled probes, two phase probes such as evaporative needle probes, air and gas cooled probes, catheter based cooling probes, Joule-Thompson gas expansion probes, and liquid gas probes.

It is noted that treatment system 100 may be controlled remotely. For example, the link between control unit 105 and treatment unit 107 may be a remote link (wired or wireless) providing control unit 105 remote control over cooling/heating element 110, treatment interface 115, probe controller 185, and probe 190.

Figure 4:
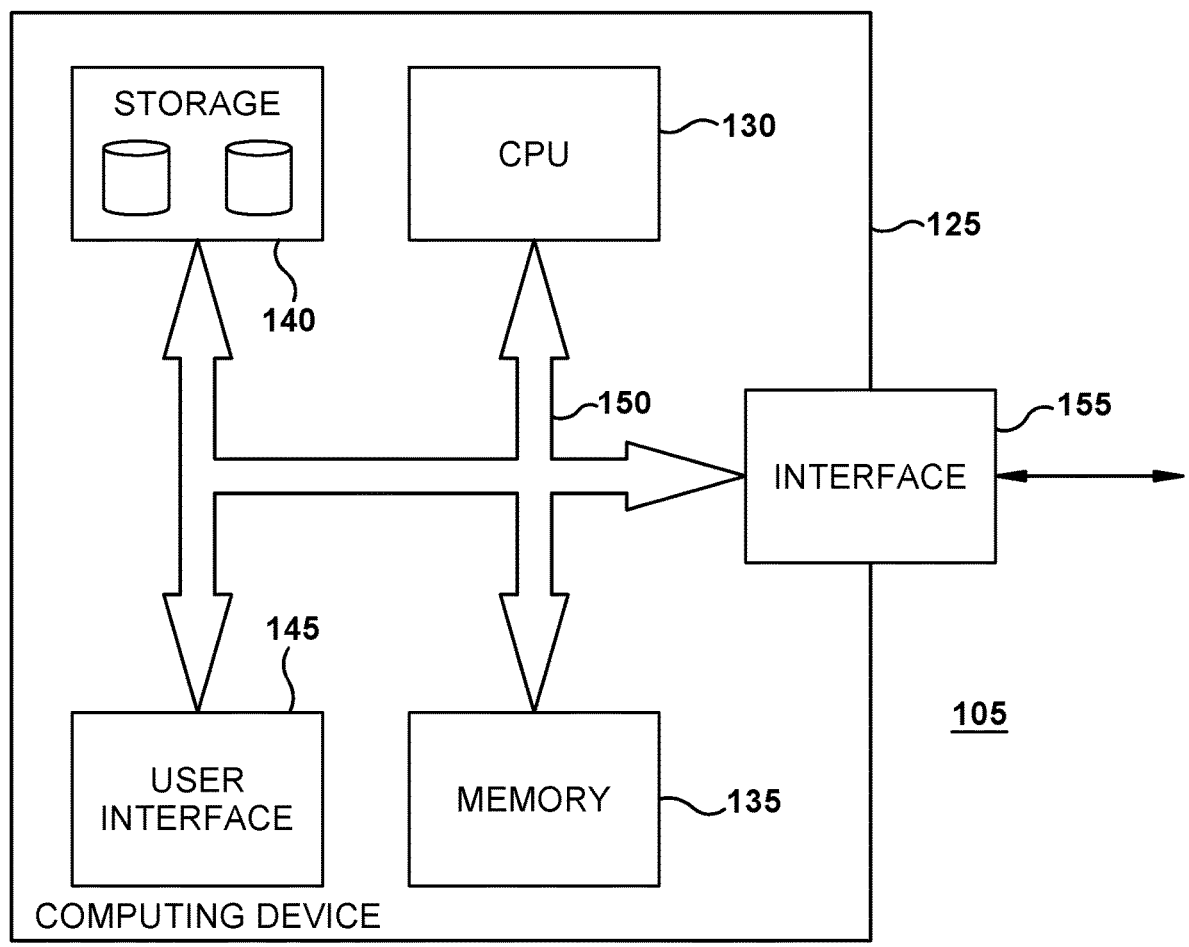
FIG. 4 provides a diagram illustrating a configuration of a control unit in accordance with another aspect of the present disclosure.

FIG. 4 is a diagram illustrating a configuration of control unit 105 in accordance with an aspect of the present disclosure. As shown in FIG. 4, control unit 105 can comprise a computing device 125, which can be a general purpose computer (such as a PC), workstation, mainframe computer system, and so forth. Computing device 125 can include a processor device (or central processing unit "CPU") 130, a memory device 135, a storage device 140, a user interface 145, a system bus 150, and a communication interface 155. CPU 130 can be any type of processing device for carrying out instructions, processing data, and so forth. Memory device 135 can be any type of memory device including any one or more of random access memory ("RAM"), read-only memory ("ROM"), Flash memory, Electrically Erasable Programmable Read Only Memory ("EEPROM"), and so forth. Storage device 140 can be any data storage device for reading/writing from/to any removable and/or integrated optical, magnetic, and/or optical-magneto storage medium, and the like (e.g., a hard disk, a compact disc-read-only memory "CD-ROM", CD-ReWritable "CD-RW", Digital Versatile Disc-ROM "DVD-ROM", DVD-RW, and so forth). Storage device 140 can also include a controller/interface (not shown) for connecting to system bus 150. Thus, memory device 135 and storage device 140 are suitable for storing data as well as instructions for programmed operations for execution on CPU 130. User interface 145 may include a touch screen, control panel, keyboard, keypad, display or any other type of interface, which can be connected to system bus 150 through a corresponding input/output device interface/adapter (not shown). Communication interface 155 may be adapted to communicate with any type of external device, including treatment unit 107. Communication interface 155 may further be adapted to communicate with any system or network (not shown), such as one or more computing devices on a local area network ("LAN"), wide area network ("WAN"), the internet, and so forth. Interface 155 may be connected directly to system bus 150, or can be connected through a suitable interface (not shown). Control unit 105 can, thus, provide for executing operations, by itself and/or in cooperation with one or more additional devices, that may include algorithms for controlling treatment unit 107 in accordance with the present disclosure. Control unit 105 may be programmed or instructed to perform these operations according to any communication protocol, programming language on any platform. Thus, the operations may be embodied in data as well as instructions stored in memory device 135 and/or storage device 140 or received at interface 155 and/or user interface 145 for execution on CPU 130.

While the above exemplary treatment system 100 is illustrative of the basic components of a system suitable for use with the present disclosure, the architecture shown should not be considered limiting since many variations of the hardware configuration are possible without departing from the present disclosure.

EXPERIMENTAL

The following Examples are for the purpose of illustration only and are not intended to limit the scope of the appended claims.

Example 1

Example 1 discloses a method used to investigate browning of adipose tissue remote to the treatment location.

Materials and Methods

Figure 5A:
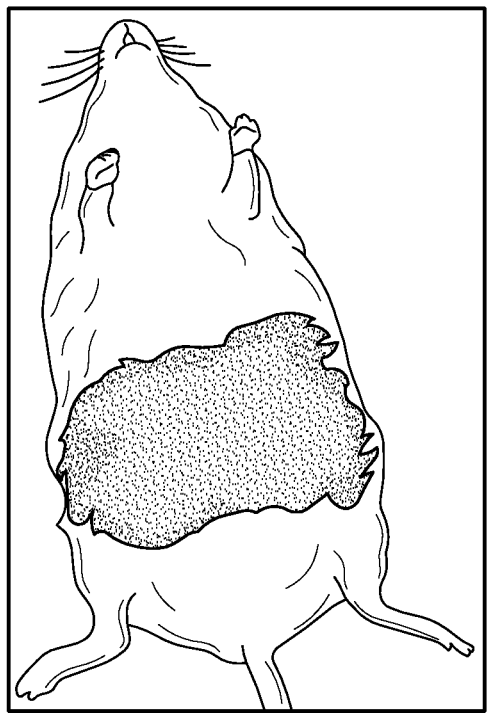
FIGS. 5(a)-(f) provide images and graphs showing a localized cooling procedure on a mouse in accordance with one aspect of the present disclosure.
Figure 5B:
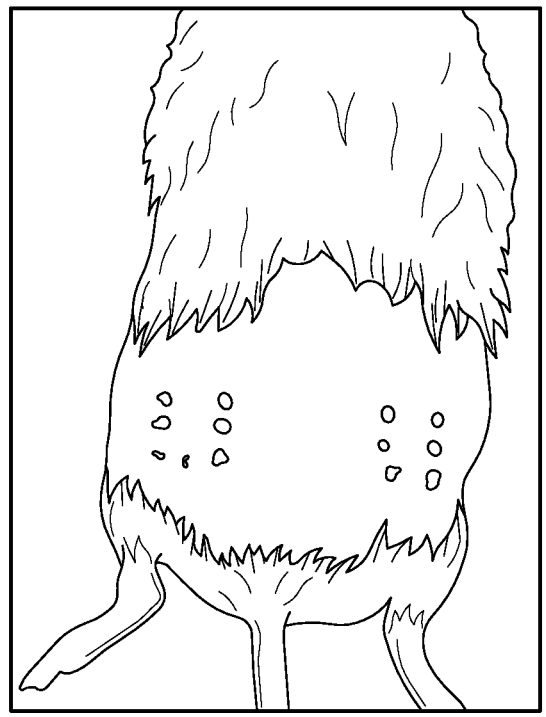
Figure 5C:
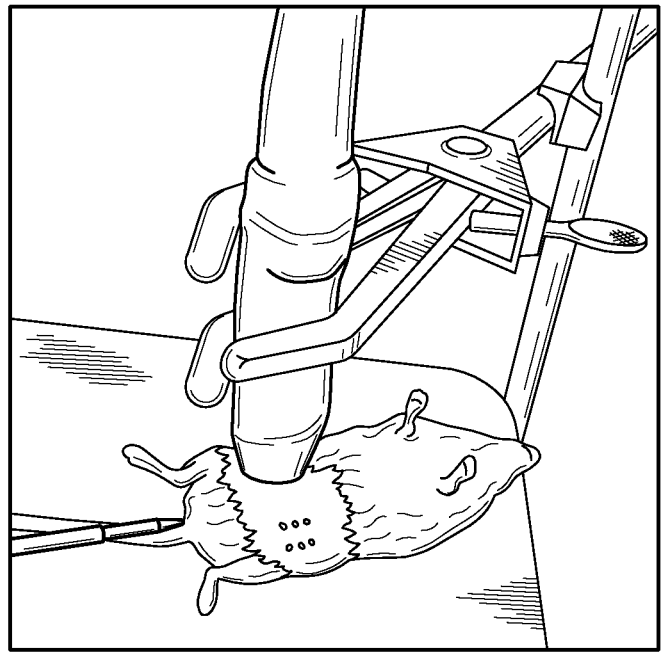
Figure 5D:
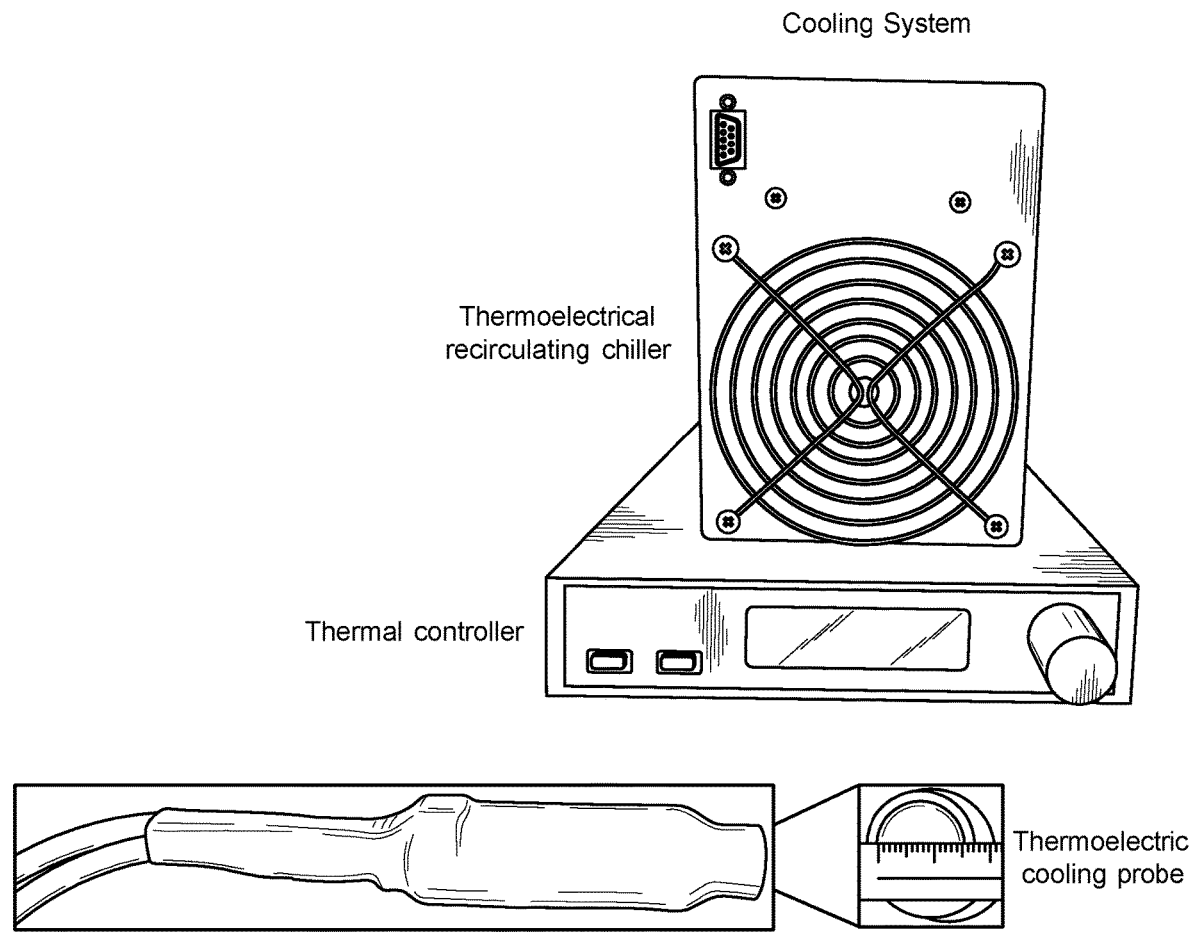
Figure 5E:
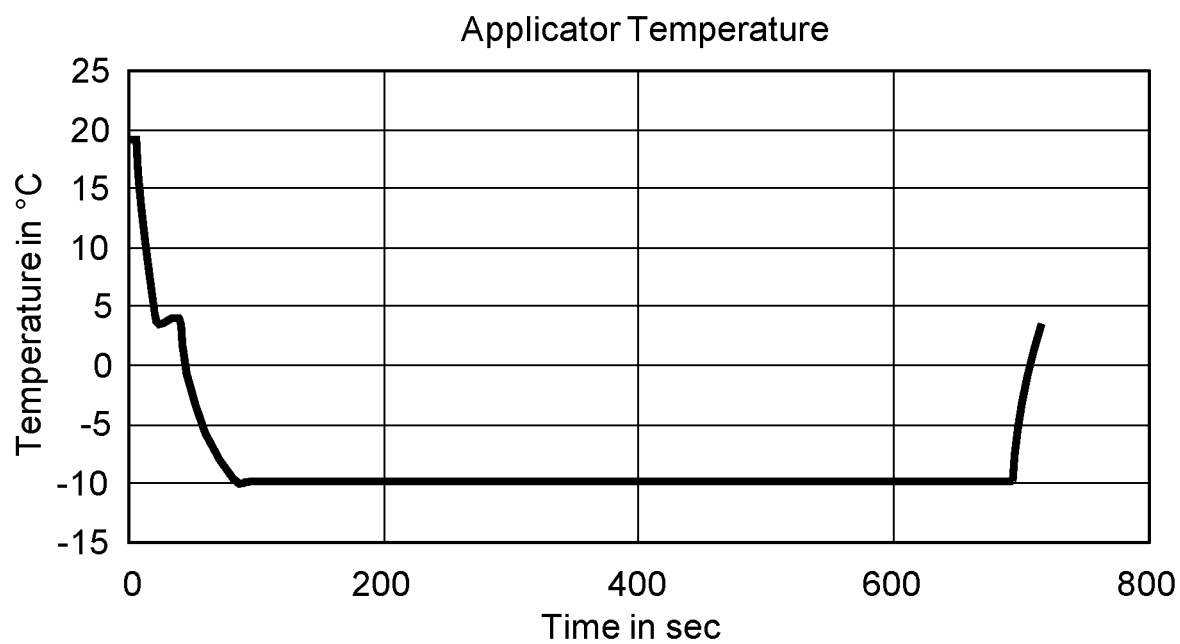

Mice and cooling procedure: Male C57BL/6J mice (22 weeks old) were anesthetized, with hair removed and tattooed at the ING areas (FIGS. 5(a)-(b)). Mice were kept on a warm pad during the procedure to maintain body temperature. A custom-built thermal control probe of 1.5 cm diameter was used to cool the right ING area of the mice at −10° C. for 10 minutes (FIGS. 5(c)-(e)). Glycerol was used as an antifreeze reagent to protect the skin.

Figure 5F:
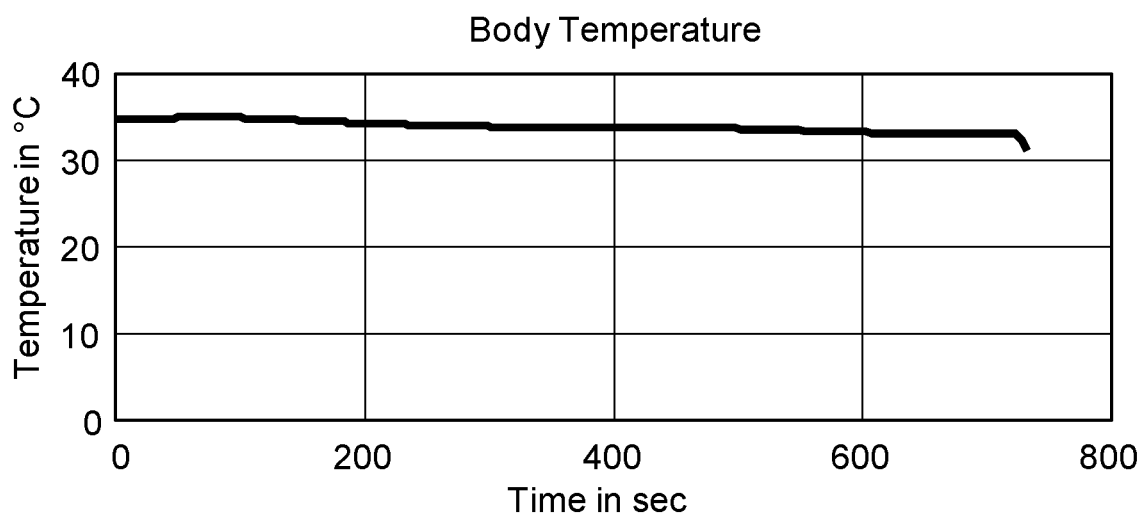

Body temperature was monitored during the experiments (FIG. 5(f)). Sham treated mice underwent the same procedure, but the temperature control-cooling probe was set at room temperature (RT). After cooling, the mice were euthanized, and samples of fat pads were dissected and analyzed for IHC and q-PCR at each of the following time points: 1 hour, day 1, day 2, day 3, day 7, and day 30.

Immunohistochemistry: Biopsies from the ING, EPI, RETRO, and BAT pads were fixed in 10% formalin, embedded in paraffin and sectioned. The paraffin sections were deparaffinized and rehydrated, followed by heat-induced antigen retrieval using sodium citrate buffer. Blocking was performed using 10% normal goat serum for 30 minutes, followed by incubation with primary antibody (Ucp1 ab10983-ABCAM) over night at 4° C. Slices were incubated with secondary antibody (Signal Stain Boost IHC detection reagent—Cell Signaling) for 30 minutes. Sections were developed in DAKO DAB for 2 minutes, counterstained in 0.5% methyl green for 10 minutes, dehydrated and mounted in Permount.

RNA isolation and q-PCR analysis: Total RNA was extracted from the ING, EPI, and BAT fat pads from control and cold treated mice. Total RNA was reverse transcribed and amplified for Ucp1 and 36B4 genes using QuantiFast SYBR green PCR master mix (Qiagen).

Figure 6A:
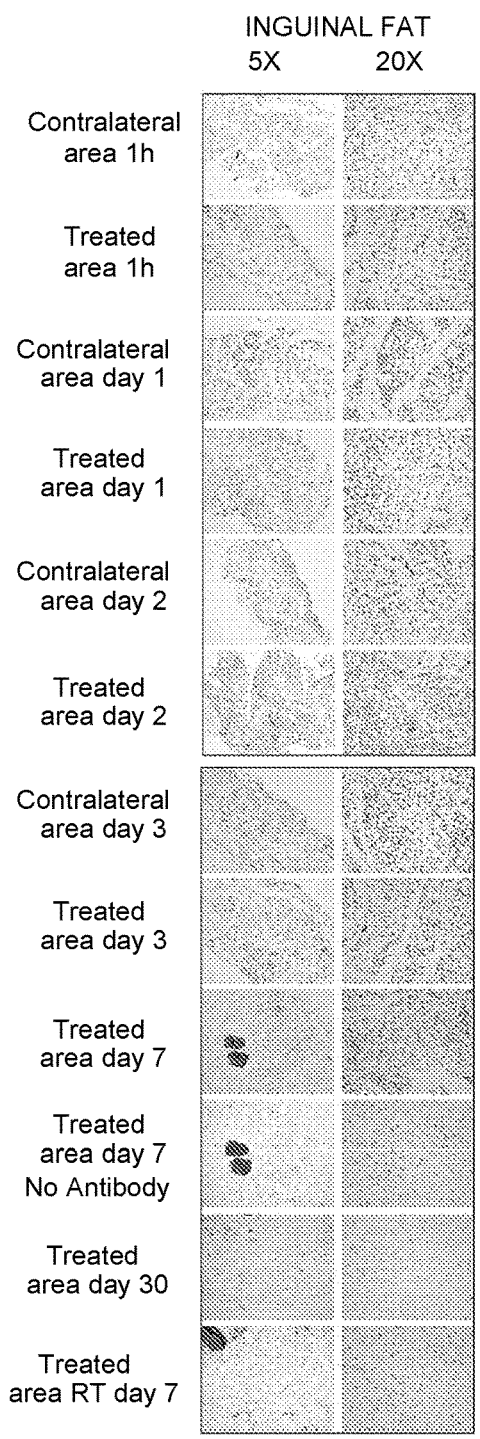
FIGS. 6(a)-(c) provide images of Ucp1 expression in mouse fat pads measured by immunocytochemistry during a time course after localized cooling.
Figure 6B:
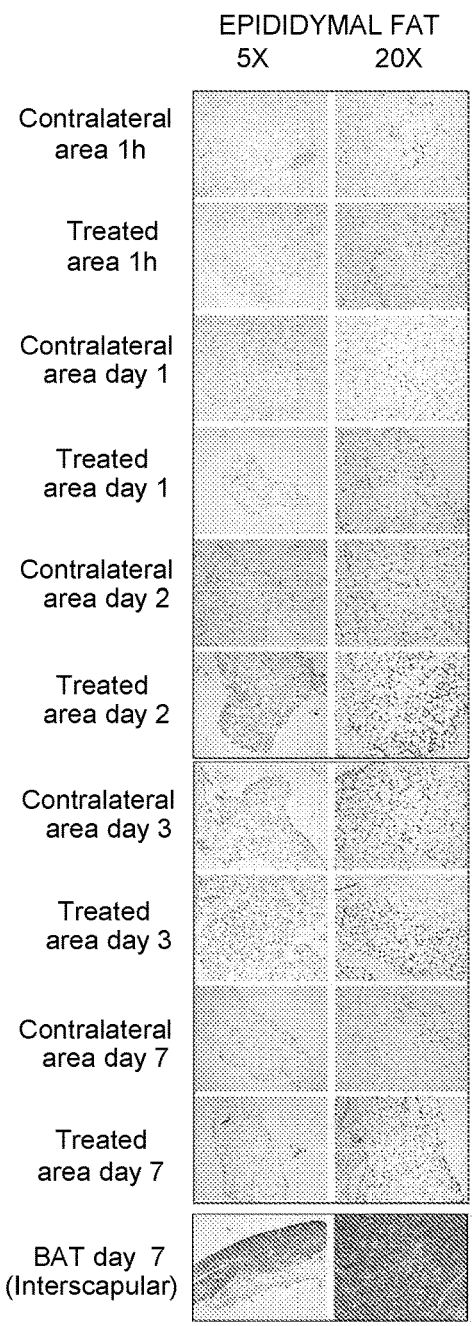
Figure 6C:
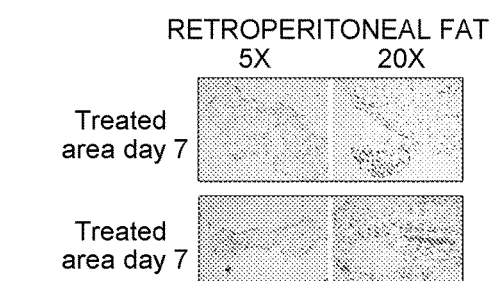

As seen in FIGS. 6(a)-(c), IHC analysis shows that Ucp1 is induced in ING, EPI, and RETRO fat fads after localized cooling exposure of the ING area of mice. Localized cooling induced browning of WAT even in areas far from the localized cold probe. Ucp1 levels were markedly induced by 1 h after expression and remained elevated in ING and EPI fat pads during the first seven days and were detected at seven days in the RETRO fat pad after localized cooling. Cells with multilocular brown morphology showed Ucp1 staining.

Figure 7A:
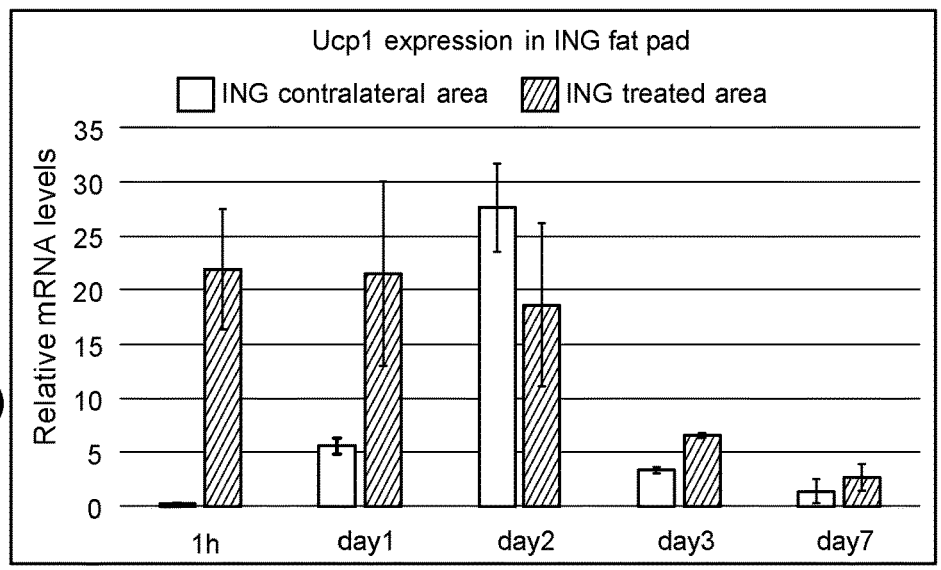
FIGS. 7(a)-(c) are graphs showing Ucp1 expression levels in mouse fat pads after localized cooling determined by real-time PCR.
Figure 7B:
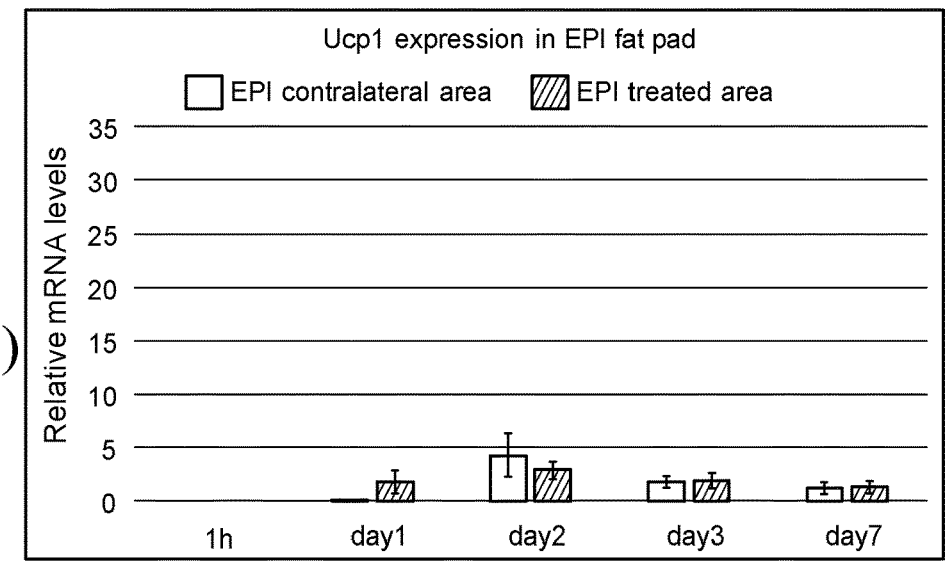
Figure 7C:
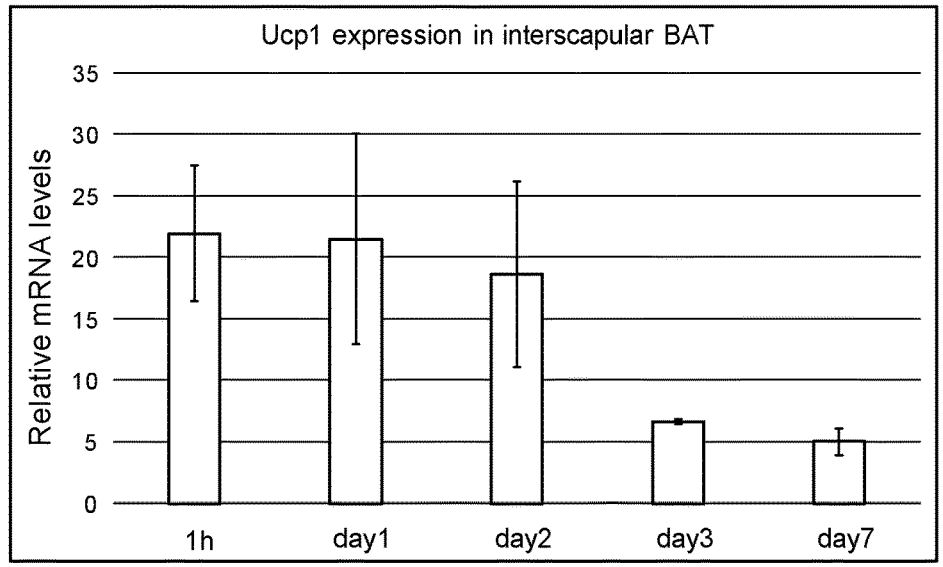

As seen in FIGS. 7(a)-(c), UCP1 mRNA expression levels were analyzed by q-PCR. Relative expression of Ucp1 was determined after normalization with 36B4 levels using the ΔΔCt method. Levels of Ucp1 were found to increase significantly during the first 3 days and decrease 7 days after cooling. Ucp1 expression levels increased approximately 20 fold in the ING and BAT fat pads and approximately 2-4 fold in the EPI fat pad.

Example 2

This Example discloses a method used to investigate browning of adipose tissue remote to the treatment location at various periods of time post treatment.
Cooling System and Experimental Procedure.

The prototype cooling device consisted of a thermoelectric recirculating chiller (Oasis 160, Solid State Cooling Systems), a thermal controller (5240 TECSource 4A/7V, Arroyo Instruments), and a custom-built thermoelectric cooling probe of 1.5 cm diameter surface cooling area. The maximum heat flux of the thermoelectric element is 3 W/cm$^2$ at ΔT=0° C. and 1.2 W/cm$^2$ at ΔT=40° C. Heat was dissipated by the recirculating chiller, and the probe temperature was kept constant through electronic control of the temperature sensors located in the cooling probe surface.

The cooling probe was cooled with the thermoelectrical recirculating chiller by circulating propylene glycol-based heat transfer fluid at 10° C. through a heat exchanger compartment connected to the thermoelectric element of the applicator Because mouse skin and subcutaneous fat are thinner than in pigs and humans, the cold exposure time was shortened as compared to those used in previous pig studies and human studies. A single cold exposure of −10° C. for 15 minutes was applied on the ING area of the mice while keeping a constant pressure upon the skin.

C57BL/J6 mice (22 weeks old) were anesthetized using ketamine/xylazine at 90 mg/9 mg/kg body weight. The mice were then shaved, depilated and tattooed at both inguinal areas. Mice were kept on a 37° C. heated pad during the procedure and core body temperature was monitored using a rectal thermometer. The right side of the inguinal area was exposed to cold using the prototype thermal control-cooling probe of ~1.5 cm of diameter for 15 minutes at −10° C. The left side of the inguinal area was used as a control. Glycerol was applied between the skin and the cooling probe to increase thermal contact and to protect the skin from freeze injury. The cooling probe was pre-cooled to 4° C. before it was applied to the inguinal area of the mice in order to increase heat flux during the initial phase of the exposure.

Mice were examined daily after cold treatment and groups of mice were euthanized for tissue collection and imaging analysis at the following time points: hour 1, day 1, day 2, day 3, day 7 and day 30. The experiment was repeated on additional cohorts of mice with the probe temperature at 0° C. and at 25° C.

Figure 8A:
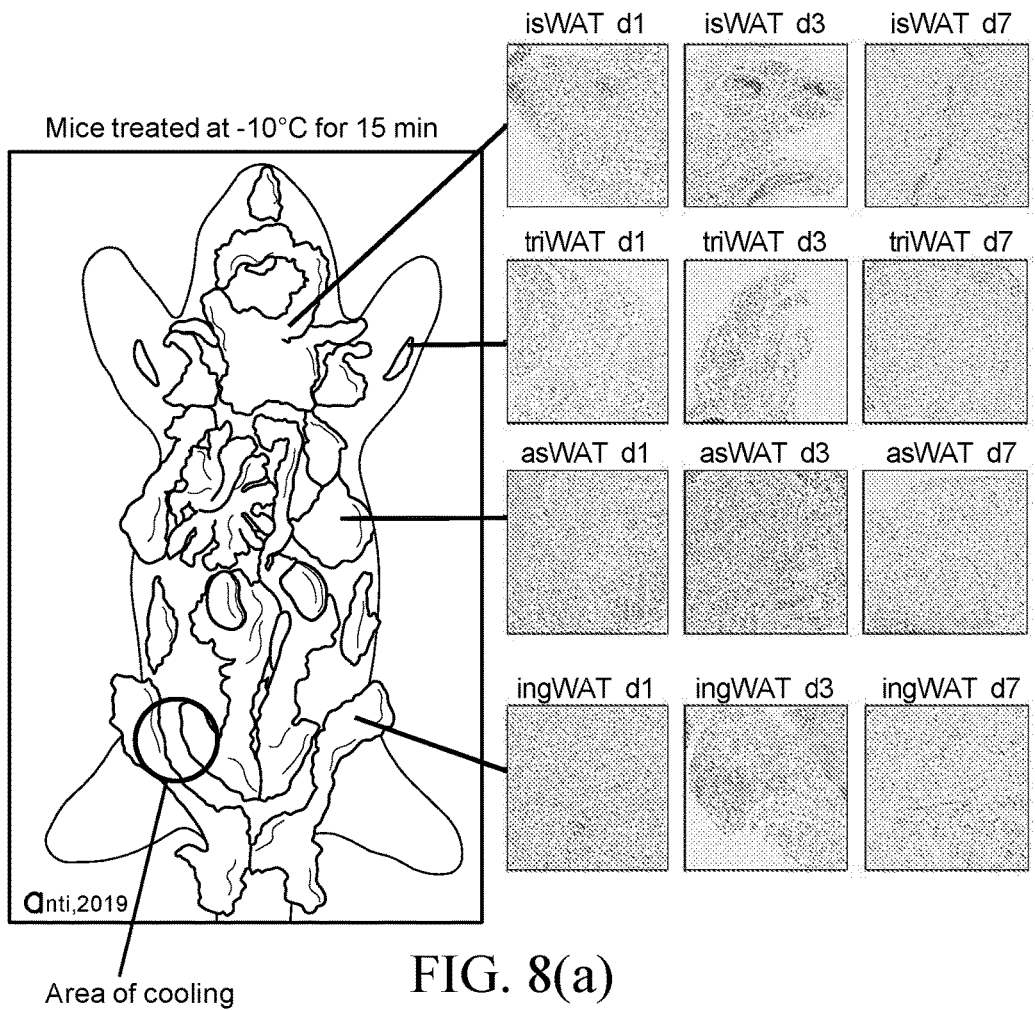
FIGS. 8(a)-(b) provide (a) images showing mouse WAT browning on day 1, day 3, and day 7 in the interscapular WAT (isWAT) of the mouse, in the triceps-associated WAT (triWAT) of the mouse, in the anterior subcutaneous WAT (asWAT) of the mouse; and in the ING WAT (ingWAT) of the mouse after the ING fat pad was cooled with an applicator cooling element temperature of −10° C. for 15 minutes, and (b) a graph showing corresponding Ucp1 activation data.
Figure 8B:
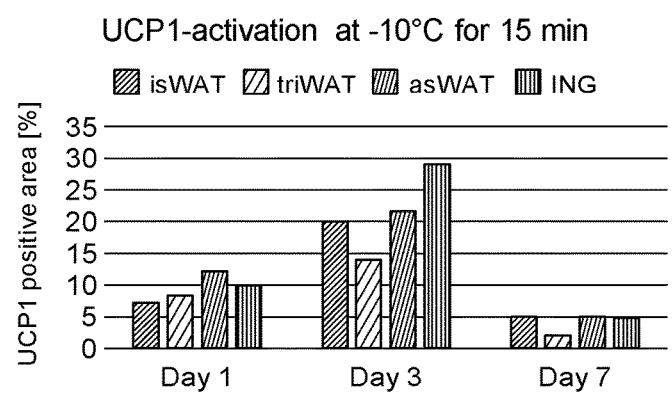
Figure 9A:
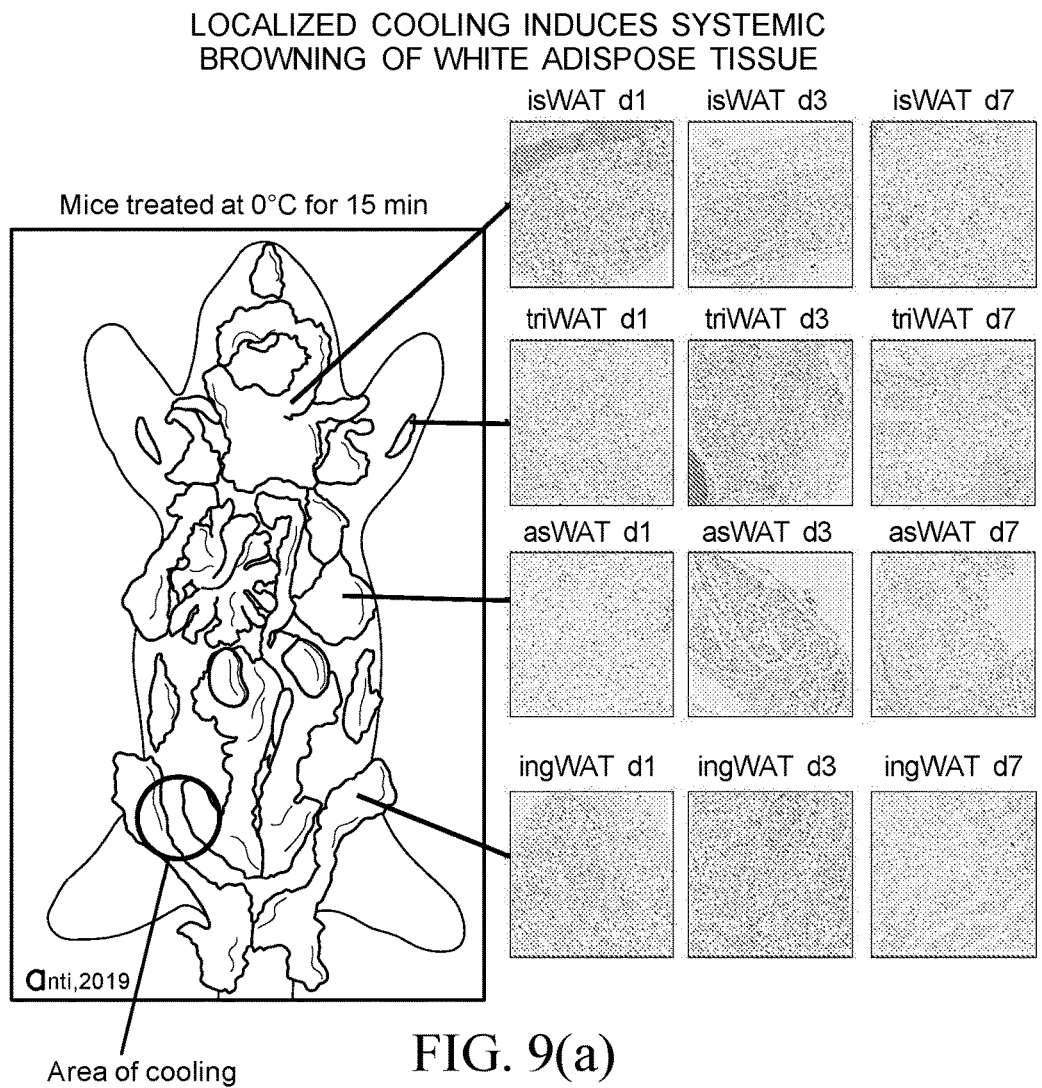
FIGS. 9(a)-(b) provide (a) images showing mouse WAT browning on day 1, day 3, and day 7 in the interscapular WAT (isWAT) of the mouse, in the triceps-associated WAT (triWAT) of the mouse, in the anterior subcutaneous WAT (asWAT) of the mouse; and in the ING WAT (ingWAT) of the mouse after the ING fat pad was cooled with an applicator cooling element temperature of 0° C. for 15 minutes, and (b) a graph showing corresponding Ucp1 activation data.
Figure 9B:
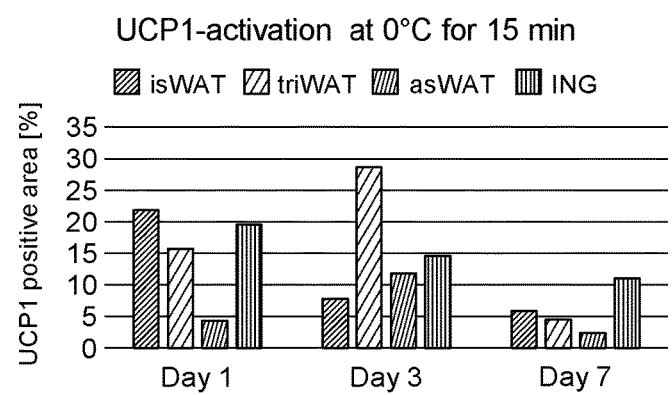
Figure 10A:
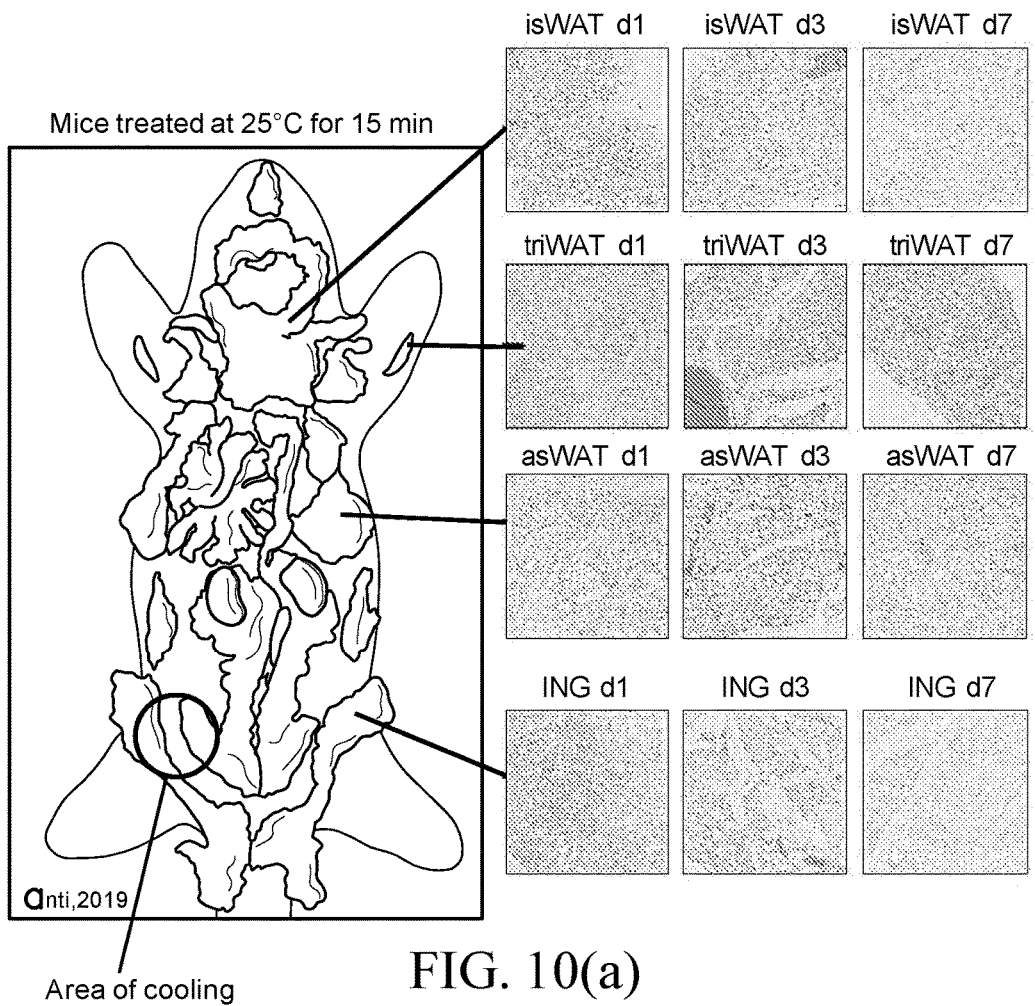
FIGS. 10(a)-(b) provide (a) images showing mouse WAT browning on day 1, day 3, and day 7 in the interscapular WAT (isWAT) of the mouse, in the triceps-associated WAT (triWAT) of the mouse, in the anterior subcutaneous WAT (asWAT) of the mouse, and in the ING WAT (ingWAT) of the mouse after the ING fat pad was cooled with an applicator cooling element temperature of 25° C. for 15 minutes, and (b) a graph showing corresponding Ucp1 activation data.
Figure 10B:
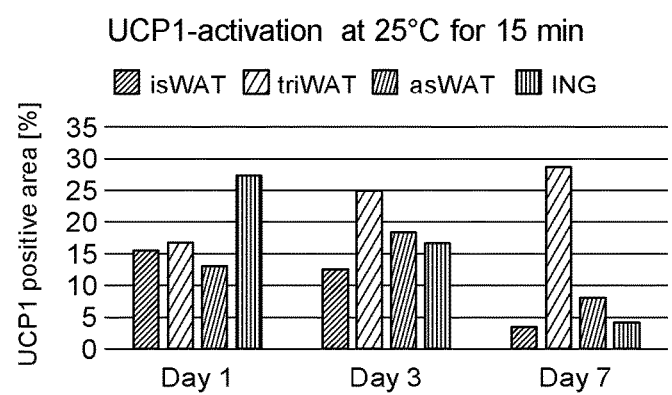

IHC analysis shows that Ucp1 is expressed in the remote isWAT, triWAT, asWAT, and ingWAT fat pads in treated mice (FIGS. 8, 9, and 10). After treatment of a localized adipose tissue area, the remote fat pads analyzed in the study show the highest elevation of Ucp1 at day 1 or day 3, with elevated values of Ucp1 expression through at least day 7.

All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls.

What is claimed is:

1. A method of inducing remote browning of adipose tissue in a subject comprising carrying out a plurality of treatments on the subject wherein the treatments comprise at least a first treatment and a second treatment, wherein the first treatment comprises cooling a first local adipose tissue deposit to a temperature of between 0° C. to 30° C. for a first period of time sufficient to induce browning of adipose tissue in one or more areas of the subject's body remote to the first local adipose tissue deposit;
    and wherein the second treatment comprises cooling a second local adipose tissue deposit to a temperature of 0° C. to 30° C. for a second period of time sufficient to induce browning of adipose tissue in one or more areas of the subject's body remote to the second local adipose tissue deposit;
    wherein the first and second local adipose tissue deposits are the same or are different; and
    wherein the second treatment is carried out 2-30 days after the day that the first treatment is carried out.

2. The method of claim 1, wherein the first and second periods of time are the same.

3. The method of claim 2, wherein the period of time is between 10 minutes and 20 minutes.

4. The method of claim 3, wherein the period of time is 10 minutes.

5. The method of claim 1, wherein the first and second local adipose tissue deposits are different.

6. The method of claim 1, wherein the first and second local adipose tissue deposits are the same.

7. The method of claim 1, wherein the second treatment is carried out 2-10 days after the first treatment is carried out.

8. The method of claim 1, wherein the second treatment is carried out 3-7 days after the first treatment is carried out.

9. The method of claim 1, wherein the method further comprises using a cooling element to cool the first and second local adipose tissue deposits.

10. The method of claim 9, wherein the method further comprises applying the cooling element to the skin of the subject.

11. The method of claim 9, wherein the method further comprises applying the cooling element directly to the adipose tissue of the first and second local adipose tissue deposits.

12. The method of claim 1, wherein the location of the first and second local adipose tissue deposits are individually selected from the abdomen, the supraclavicular region, the dorsocervical region, the cervical region, the flanks, the buttocks, the lower torso, the hips, and the upper thighs.

13. The method of claim 1, wherein browning of adipose tissue continues for at least 24 hours after treatment.

14. The method of claim 1, wherein the browning of adipose tissue continues for at least 72 hours after treatment.

15. The method of claim 1, wherein the browning of adipose tissue continues for at least 168 hours after treatment.

16. The method of claim 1, wherein the method is used to change the metabolic rate of the subject.

17. The method of claim 1, wherein the method is used to induce weight loss in the subject.

18. The method of claim 1, wherein the method is used to treat cardiovascular disease.

19. The method of claim 1, wherein the method is used to treat obesity.

20. The method of claim 1, wherein the method is used to improve one or more of insulin response, hypercholesterolemia, and glucose levels.

21. The method of claim 1, wherein the method is carried out until a predetermined outcome is achieved.

22. The method of claim 1, wherein the cooling element comprises a thermoelectric cooler.

23. The method of claim 1, wherein the cooling element comprises a cooling probe inserted in the adipose tissue deposit.

\* \* \* \* \*